US012082867B2

(12) United States Patent
Siazon et al.

(10) Patent No.: US 12,082,867 B2
(45) Date of Patent: *Sep. 10, 2024

(54) ELECTROSURGICAL SYSTEM

(71) Applicant: Applied Medical Resources Corporation, Rancho Santa Margarita, CA (US)

(72) Inventors: Kevin Siazon, Las Vegas, NV (US); Ryan Pope, Rancho Santa Margarita, CA (US); Vincent Rodriguez, Rancho Santa Margarita, CA (US); Devon Augustus, Rancho Santa Margarita, CA (US); Duy Nguyen, Rancho Santa Margarita, CA (US); Patrick Elliott, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 478 days.

This patent is subject to a terminal disclaimer.

(21) Appl. No.: 17/532,926

(22) Filed: Nov. 22, 2021

(65) Prior Publication Data
US 2022/0079651 A1   Mar. 17, 2022

Related U.S. Application Data

(63) Continuation of application No. 16/194,055, filed on Nov. 16, 2018, now Pat. No. 11,207,123.

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1445* (2013.01); *A61B 2018/00607* (2013.01);
(Continued)

(58) Field of Classification Search
CPC ............ A61B 18/1206; A61B 18/1445; A61B 2018/00607; A61B 2018/0063;
(Continued)

(56) References Cited

U.S. PATENT DOCUMENTS

| 4,289,135 A | 9/1981 | Nordenström et al. |
| 4,318,490 A | 3/1982 | Oosten |

(Continued)

OTHER PUBLICATIONS

European Patent Office, The International Search Report and Written Opinion for International Application No. PCT/US2018/061646, entitled "Electrosurgical System," mailed May 7, 2019, 12 pgs.

*Primary Examiner* — Daniel W Fowler
(74) *Attorney, Agent, or Firm* — Thomas Nguyen; Patrick Ikehara

(57) ABSTRACT

An electrosurgical system is provided and includes a bipolar electrosurgical instrument and an electrosurgical generator. The bipolar electrosurgical instrument is arranged to seal and cut tissue captured between jaws of the instrument. The jaws include particularly positioned, shaped and/or oriented electrodes to perform the sealing of tissue. The electrosurgical generator is arranged to supply RF energy through the instrument, monitor the supplied RF energy and adjust or terminate the supplied RF energy to optimally seal the tissue.

18 Claims, 12 Drawing Sheets

(52) U.S. Cl.
CPC ............... *A61B 2018/0063* (2013.01); *A61B 2018/00702* (2013.01); *A61B 2018/00791* (2013.01); *A61B 2018/00827* (2013.01); *A61B 2018/00869* (2013.01); *A61B 2018/00875* (2013.01); *A61B 2018/00892* (2013.01); *A61B 2018/1253* (2013.01); *A61B 2018/126* (2013.01); *A61B 2018/1412* (2013.01); *A61B 2018/1425* (2013.01); *A61B 2018/1455* (2013.01); *A61B 2018/146* (2013.01); *A61B 2018/1462* (2013.01)

(58) Field of Classification Search
CPC .......... A61B 2018/00678; A61B 2018/00708; A61B 2018/00767; A61B 2018/00791; A61B 2018/00827; A61B 2018/00869; A61B 2018/00875; A61B 2018/00886; A61B 2018/00892; A61B 2018/1253; A61B 2018/126; A61B 2018/1412; A61B 2018/1425; A61B 2018/1455; A61B 2018/146; A61B 2018/1462
See application file for complete search history.

(56) References Cited

U.S. PATENT DOCUMENTS

| | | | |
|---|---|---|---|
| 4,378,801 A | 4/1983 | Oosten | |
| 4,531,524 A | 7/1985 | Mioduski | |
| 5,318,563 A | 6/1994 | Malis et al. | |
| 5,974,342 A | 10/1999 | Petrofsky | |
| 6,123,702 A | 9/2000 | Swanson et al. | |
| 6,162,217 A | 12/2000 | Kannenberg et al. | |
| 6,183,468 B1 | 2/2001 | Swanson et al. | |
| 6,245,065 B1 | 6/2001 | Panescu et al. | |
| 6,275,786 B1 | 8/2001 | Daners | |
| 6,398,779 B1 | 6/2002 | Buysse et al. | |
| 6,488,679 B1 | 12/2002 | Swanson et al. | |
| 6,494,880 B1 | 12/2002 | Swanson et al. | |
| 6,796,981 B2 | 9/2004 | Wham et al. | |
| 6,939,346 B2 | 9/2005 | Kannenberg et al. | |
| 7,303,557 B2 | 12/2007 | Wham et al. | |
| 7,364,577 B2 | 4/2008 | Wham et al. | |
| 7,582,084 B2 | 9/2009 | Swanson et al. | |
| 7,972,328 B2 | 7/2011 | Wham et al. | |
| 8,147,485 B2 | 4/2012 | Wham et al. | |
| 8,216,223 B2 | 7/2012 | Wham et al. | |
| 8,287,528 B2 | 10/2012 | Wham et al. | |
| 8,419,727 B2 | 4/2013 | Koss et al. | |
| 8,486,060 B2 | 7/2013 | Kotmel et al. | |
| 8,591,506 B2 | 11/2013 | Wham et al. | |
| 8,685,016 B2 | 4/2014 | Wham et al. | |
| 8,715,278 B2 | 5/2014 | Toth et al. | |
| 8,827,992 B2 | 9/2014 | Koss et al. | |
| 8,888,770 B2 | 11/2014 | Eder et al. | |
| 8,939,971 B2 | 1/2015 | Truckai et al. | |
| 9,161,813 B2 | 10/2015 | Benamou | |
| 9,186,200 B2 | 11/2015 | Unger et al. | |
| 9,358,063 B2 | 6/2016 | Marion | |
| 9,375,270 B2 | 6/2016 | Wham et al. | |
| 9,375,271 B2 | 6/2016 | Wham et al. | |
| 2004/0167508 A1 | 8/2004 | Wham et al. | |
| 2005/0203504 A1* | 9/2005 | Wham | A61B 18/1442 606/34 |
| 2010/0087894 A1* | 4/2010 | Kabaya | A61B 18/1206 607/50 |
| 2011/0144635 A1 | 6/2011 | Harper et al. | |
| 2012/0078139 A1 | 3/2012 | Aldridge et al. | |
| 2015/0025529 A1 | 1/2015 | Koss et al. | |
| 2016/0045248 A1 | 2/2016 | Unger et al. | |
| 2016/0310207 A1* | 10/2016 | Honda | A61B 18/1445 |
| 2016/0367308 A1 | 12/2016 | Takami et al. | |
| 2017/0027633 A1 | 2/2017 | Wham et al. | |
| 2017/0065339 A1 | 3/2017 | Mickelsen | |
| 2017/0196621 A1* | 7/2017 | Wilson | A61B 18/1445 |

\* cited by examiner

ELECTROSURGICAL SYSTEM

CROSS REFERENCE TO RELATED APPLICATIONS

This application is a continuation of U.S. patent application Ser. No. 16/194,055 entitled "Electrosurgical System," filed Nov. 16, 2018, which is hereby incorporated herein by reference in its entirety.

BACKGROUND

The present application relates generally to electrosurgical systems and methods and more particularly relates to electrosurgical generators and associated instruments for sealing and cutting tissue.

Electrosurgical devices or instruments have become available that use electrical energy to perform certain surgical tasks. Typically, electrosurgical instruments are surgical instruments such as graspers, scissors, tweezers, blades, and/or needles that include one or more electrodes that are configured to be supplied with electrical energy from an electrosurgical generator. The electrical energy can be used to coagulate, fuse, or cut tissue to which it is applied.

Electrosurgical instruments typically fall within two classifications: monopolar and bipolar. In monopolar instruments, electrical energy is supplied to one or more electrodes on the instrument with high current density while a separate return electrode is electrically coupled to a patient and is often designed to minimize current density. Monopolar electrosurgical instruments can be useful in certain procedures, but can include a risk of certain types of patient injuries such as electrical burns often at least partially attributable to functioning of the return electrode. In bipolar electrosurgical instruments, one or more electrodes are electrically coupled to a source of electrical energy of a first polarity and one or more other electrodes is electrically coupled to a source of electrical energy of a second polarity opposite the first polarity. Bipolar electrosurgical instruments, which operate without separate return electrodes, can deliver electrical signals to a focused tissue area with reduced risks.

Even with the relatively focused surgical effects of bipolar electrosurgical instruments, however, surgical outcomes are often highly dependent on surgeon skill. For example, thermal tissue damage and necrosis can occur in instances where electrical energy is delivered for a relatively long duration or where a relatively high-powered electrical signal is delivered even for a short duration. The rate at which a tissue will achieve the desired fusing, sealing or cutting effect upon the application of electrical energy varies based on the tissue type and can also vary based on pressure applied to the tissue by an electrosurgical device. However, it can be difficult for a surgeon to assess how quickly a mass of combined tissue types grasped in an electrosurgical instrument will be sealed a desirable amount.

SUMMARY

In accordance with various embodiments, an electrosurgical instrument is provided that is configured to fuse and cut tissue. In various embodiments, the electrosurgical device or instrument includes a first jaw and a second jaw opposing the first jaw to grasp tissue between the first and second jaws. The first jaw includes an electrode and the second jaw includes an electrode. The electrodes of the first and second jaws are arranged to seal tissue between the first and second jaws using radio frequency energy.

In accordance with various embodiments, an electrosurgical system is provided and comprises an electrosurgical instrument having a handle assembly and jaws connected to the handle assembly and an electrosurgical generator removably coupled to the electrosurgical instrument. The electrosurgical generator is configured to supply RF energy to the electrosurgical instrument starting at a predefined first voltage and increasing to a predefined second voltage within a predetermined first time period. In various embodiments, the generator is configured to adjust voltage of the supplied RF energy to start at a predefined third voltage after an expiration of the predetermined first time period and/or after voltage of the supplied RF energy reaches the predefined second voltage. In various embodiments, the generator is configured to adjust voltage of the supplied RF energy to be held constant at a predefined voltage or at the voltage once and/or after the expiration of a predetermined second time period.

In accordance with various embodiments, an electrosurgical system for sealing tissue is provided. The system in various embodiments comprises an electrosurgical generator and an electrosurgical instrument or device. The generator includes an RF amplifier and a controller. The RF amplifier supplies RF energy through a removably coupled electrosurgical instrument configured to seal tissue with only RF energy. The controller and/or RF sense are arranged to monitor and/or measure the supplied RF energy and/or components thereof. In various embodiments, the controller signals the RF amplifier to adjust, e.g., increase, hold, decrease and/or stop, voltage of the supplied RF energy at predetermined points or conditions of a sealing cycle. In various embodiments, the controller signals the RF amplifier to halt the supplied RF energy or initiate termination of the supplied RF energy from the RF amplifier.

In various embodiments, an electrosurgical generator is provided and comprises an RF amplifier configured to supply RF energy to an electrosurgical instrument in which the supplied RF energy having a voltage spike. In various embodiments, an electrosurgical generator is provided and is configured to supply RF energy to an electrosurgical instrument based on a control script provided by the electrosurgical instrument to adjust voltage of the supplied RF energy based on predefined conditions included in the control script. In various embodiments, an electrosurgical instrument is provide and configured to house and provide a control script to an electrosurgical generator in which the control script is configured to cause the electrosurgical generator to adjust voltage of the supplied RF energy based on predefined conditions identified in the control script.

The various features and embodiments provided throughout can be used alone, or in combination with other features and/or embodiments other than as expressly described and although specific combinations of embodiments and features or aspects of various embodiments may not be explicitly described such combinations however are contemplated and within the scope of the present inventions. Many of the attendant features of the present inventions will be more readily appreciated as the same becomes better understood by reference to the foregoing and following description and considered in connection with the accompanying drawings.

BRIEF DESCRIPTION OF THE DRAWINGS

The present inventions may be better understood taken in connection with the accompanying drawings in which the reference numerals designate like parts throughout the figures thereof.

DETAILED DESCRIPTION

Generally, an electrosurgical system is provided that includes an electrosurgical generator and a removably coupled electrosurgical instrument that are configured to optimally seal or fuse tissue. The RF energy is supplied by the electrosurgical generator that is arranged to provide the appropriate RF energy to seal the tissue. The generator in accordance with various embodiments determines the appropriate RF energy and the appropriate manner to deliver the RF energy for the particular connected electrosurgical instrument, the particular tissue in contact with the instrument and/or a particular surgical procedure. Operationally, RF sealing or fusing of tissue between the jaws is provided to decrease sealing time and/or thermal spread.

In accordance with various embodiments, the electrosurgical system applies RF energy having a high voltage for a short duration to provide an RF energy spike. Subsequently, the electrosurgical system reduces the voltage of the supplied RF energy while continuing to apply RF energy. The electrosurgical system also continuously monitors the supplied RF energy to detect short or open conditions. The system also determines the shift from the high voltage RF energy spike to the reduced voltage RF energy supply and determination of tissue or vessel fusion or sealing, thereby ceasing or terminating the supply of RF energy.

Figure 1:
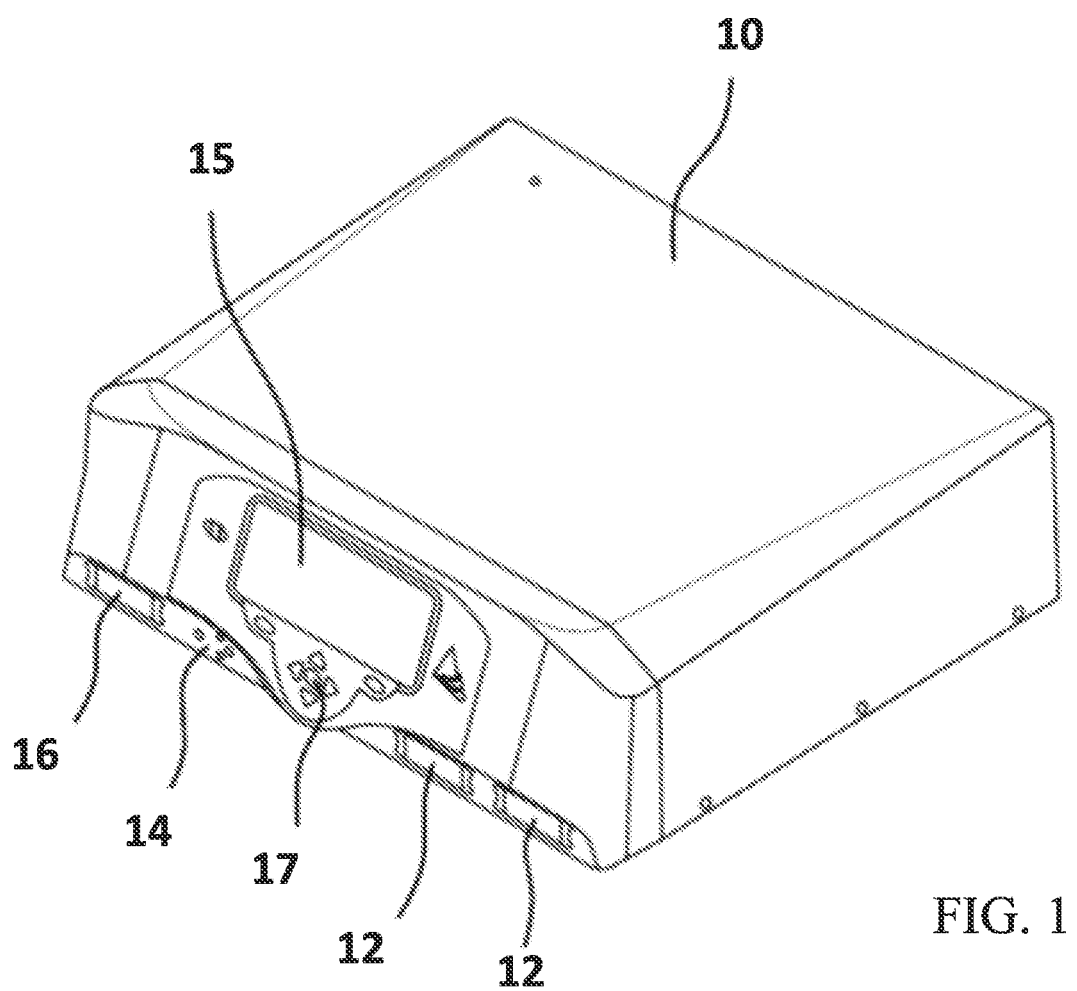
FIG. 1 is a perspective view of an electrosurgical system in accordance with various embodiments of the present invention.
Figure 2:
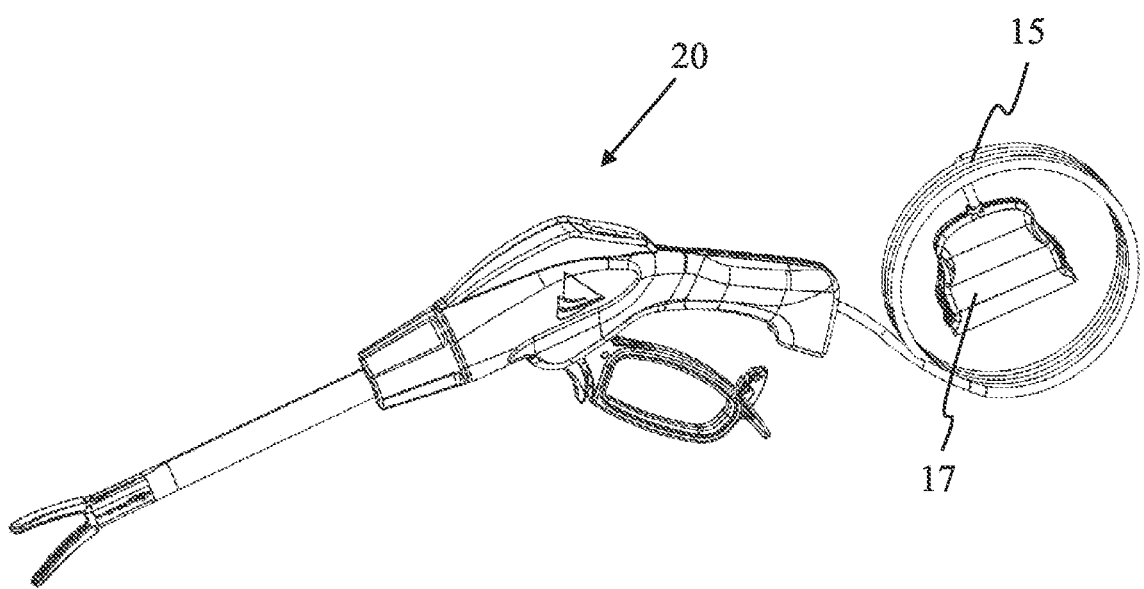
FIGS. 2-3 are perspective views of an electrosurgical instrument in accordance with various embodiments of the present invention.

Referring to FIGS. 1-2, an exemplary embodiment of electrosurgical system is illustrated including an electrosurgical generator 10 and a removably connectable electrosurgical instrument 20. The electrosurgical instrument 20 can be electrically coupled to the generator via a cabled connection 30 to a tool or device port 12 on the generator. The electrosurgical instrument 20 may include audio, tactile and/or visual indicators to apprise a user of a particular predetermined status of the instrument such as a start and/or end of a fusion or cut operation. In other embodiments, the electrosurgical instrument 20 can be reusable and/or connectable to another electrosurgical generator for another surgical procedure. In some embodiments, a manual controller such as a hand or foot switch can be connectable to the generator and/or instrument to allow predetermined selective control of the instrument such as to commence a fusion or cut operation.

In accordance with various embodiments, the electrosurgical generator 10 is configured to generate radiofrequency (RF) electrosurgical energy and to receive data or information from the electrosurgical instrument 20 electrically coupled to the generator. The generator 10 in one embodiment outputs RF energy (e.g., 375 VA, 150 V, 5 A at 350 kHz) and in one embodiment is configured to measure current and/or voltage of the RF energy and/or to calculate power of the RF energy or a phase angle or difference between RF output voltage and RF output current during activation or supply of RF energy. The generator regulates voltage, current and/or power and monitors RF energy output (e.g., voltage, current, power and/or phase). In one embodiment, the generator 10 stops RF energy output under predefined conditions such as when a device switch is de-asserted (e.g., fuse button released), a time value is met, and/or active phase angle, current, voltage or power and/or changes thereto is greater than, less than or equal to a stop value, threshold or condition and/or changes thereto.

The electrosurgical generator 10 comprises at least one advanced bipolar tool port 12, a standard bipolar tool port 16, and an electrical power port 14. In other embodiments, electrosurgical units can comprise different numbers of ports. For example, in some embodiments, an electrosurgical generator can comprise more or fewer than two advanced bipolar tool ports, more or fewer than the standard bipolar tool port, and more or fewer than the power port. In one embodiment, the electrosurgical generator comprises only two advanced bipolar tool ports.

In accordance with various embodiments, each advanced bipolar tool port 12 is configured to be coupled to an electrosurgical instrument having an attached or integrated memory module. The standard bipolar tool port 16 is configured to receive a non-specialized bipolar electrosurgical tool that differs from the advanced bipolar electrosurgical instrument connectable to the advanced bipolar tool port 12. The electrical power port 14 is configured to receive or be connected to a direct current (DC) accessory device that differs from the non-specialized bipolar electrosurgical tool and the advanced electrosurgical instrument. The electrical power port 14 is configured to supply direct current voltage. For example, in some embodiments, the power port 14 can provide approximately 12 Volts DC. The power port 14 can be configured to power a surgical accessory, such as a respirator, pump, light, or another surgical accessory. Thus, in addition to replacing electrosurgical generator for standard or non-specialized bipolar tools, the electrosurgical generator can also replace a surgical accessory power supply. In some embodiments, replacing presently-existing generators and power supplies with the electrosurgical generator can reduce the amount of storage space required on storage racks cards or shelves in the number of mains power cords required in a surgical workspace.

In accordance with various embodiments, the electrosurgical generator 10 can comprise a display 15. The display can be configured to indicate the status of the electrosurgical system including, among other information, the status of the one or more electrosurgical instruments and/or accessories, connectors or connections thereto.

The electrosurgical generator in accordance with various embodiments can comprise a user interface such as a plurality of buttons 17. The buttons can allow user interaction with the electrosurgical generator such as, for example, requesting an increase or decrease in the electrical energy supplied to one or more instruments coupled to the electrosurgical generator. In other embodiments, the display 15 can be a touch screen display thus integrating data display and user interface functionalities. In one embodiment, the electrosurgical tool or instrument 20 can further comprise of one or more memory modules. In some embodiments, the memory comprises operational data concerning the instrument and/or other instruments. For example, in some embodiments, the operational data may include information regarding electrode configuration/reconfiguration, the instrument uses, operational time, voltage, power, phase and/or current settings, and/or particular operational states, conditions, scripts, processes or procedures. In one embodiment, the generator initiates reads and/or writes to the memory module.

In accordance with various embodiments, the generator provides the capability to read the phase difference or phase angle between the voltage and current of the RF energy sent through the connected electrosurgical instrument while RF energy is active. While tissue is being fused, phase readings are used to detect different states during the fuse or seal and cut process.

The generator in accordance with various embodiments does not monitor or control current, power or impedance. The generator regulates voltage and can adjust voltage. Electrosurgical power delivered is a function of applied voltage, current and tissue impedance. The generator through the regulation of voltage can affect the electrosurgical power being delivered. However, by increasing or decreasing voltage, delivered electrosurgical power does not necessarily increase or decrease. Power reactions are caused by the power interacting with the tissue or the state of the tissue without any control by a generator other than by the generator supplying power.

The generator once it starts to deliver electrosurgical power does so continuously, e.g., every 150 ms, until a fault occurs or a specific parameter is reached. In one example, the jaws of the electrosurgical instrument can be opened and thus compression relieved at any time before, during and after the application of electrosurgical power. The generator in one embodiment also does not pause or wait a particular duration or a predetermined time delay to commence termination of the electrosurgical energy.

Figure 3:
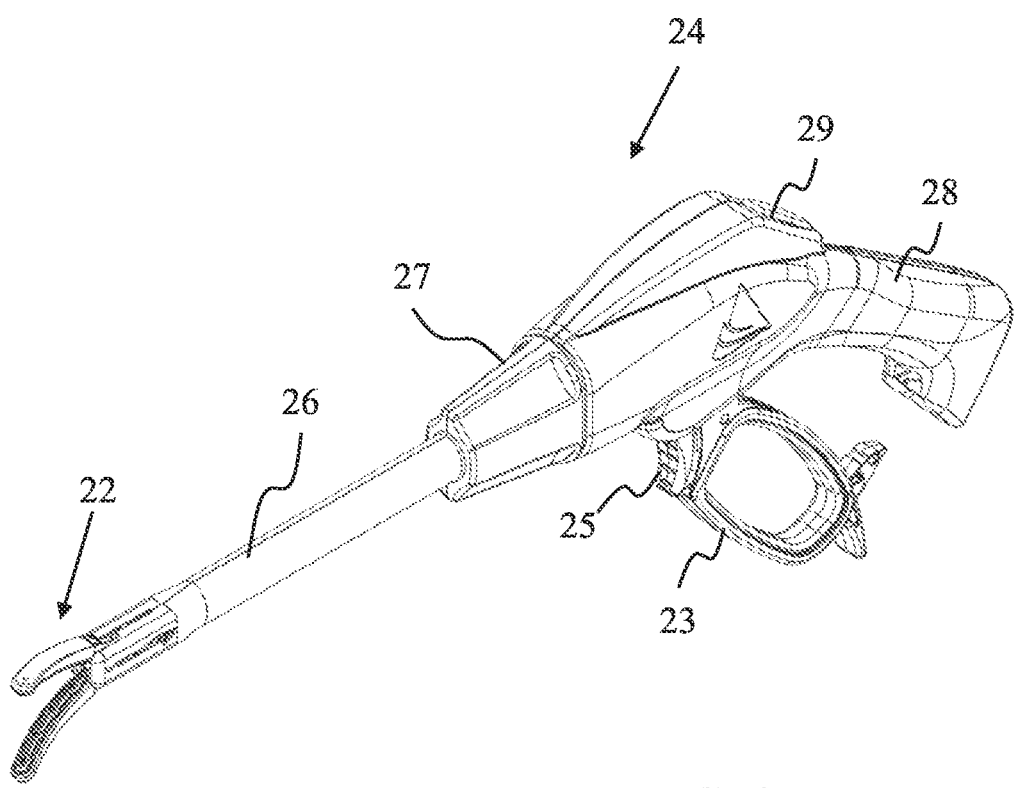
Figure 4:
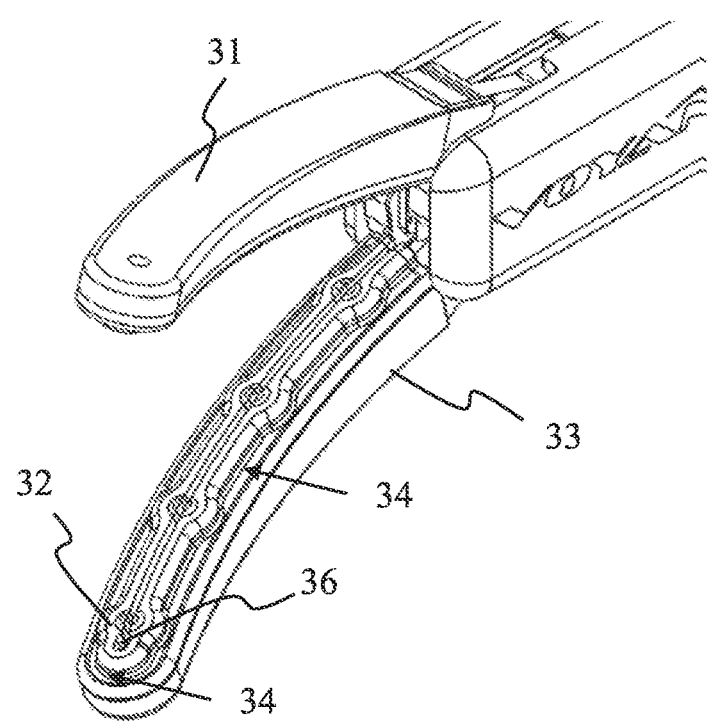
FIGS. 4-5 are perspective views of a distal end of the electrosurgical instrument in accordance with various embodiments of the present invention.
Figure 5:
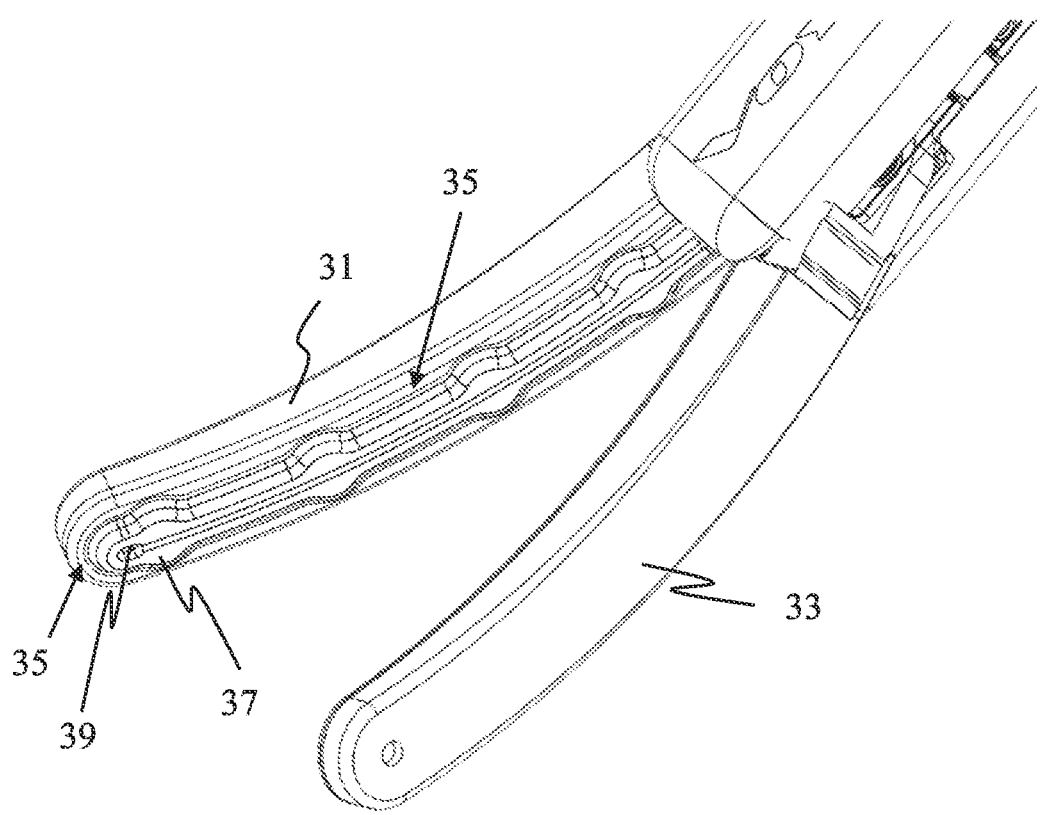
Figure 6:
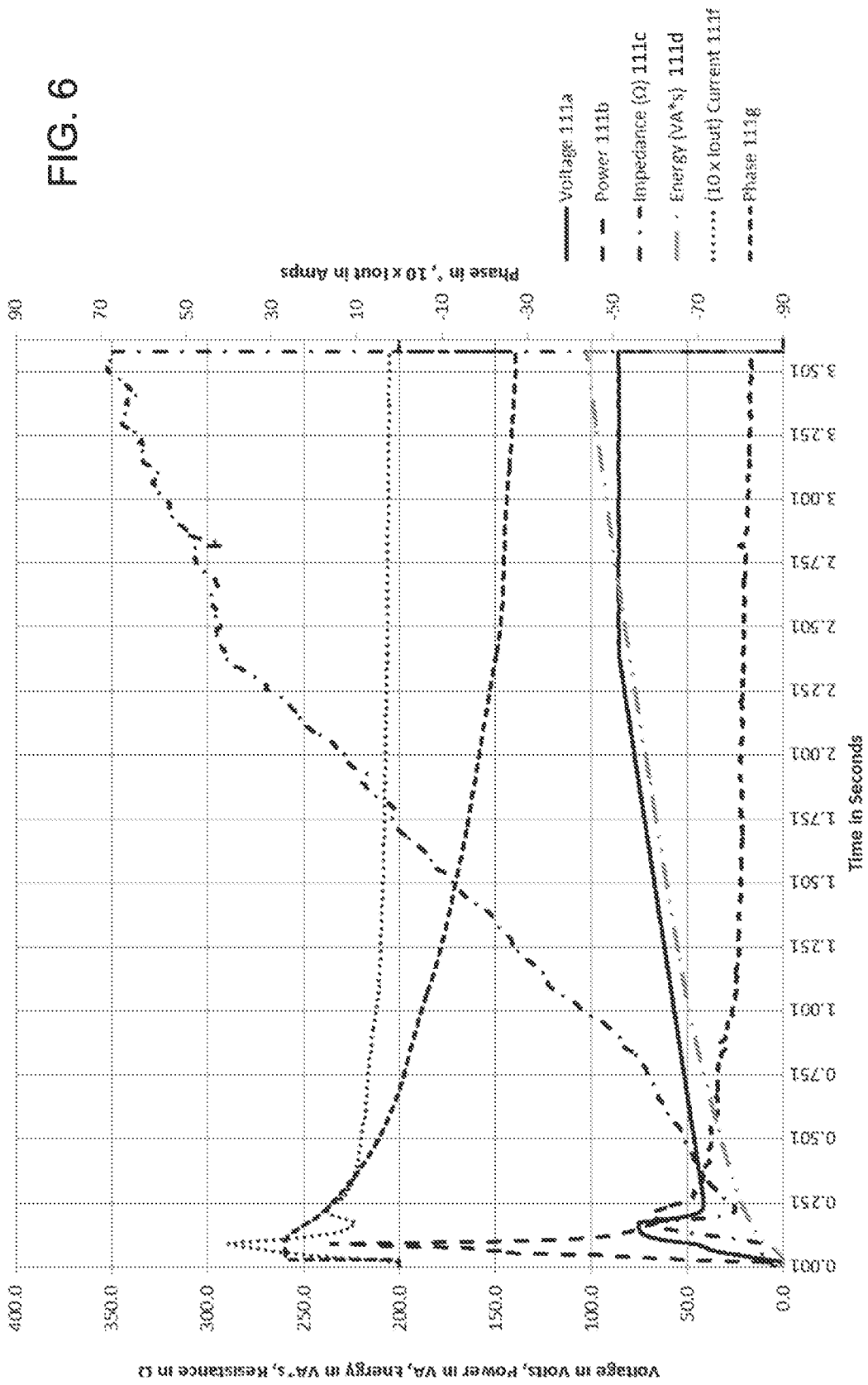
FIGS. 6-9 are graphical representations of samples of experimental data for a sealing process with an electrosurgical system in accordance with various embodiments of the present invention.
Figure 7:
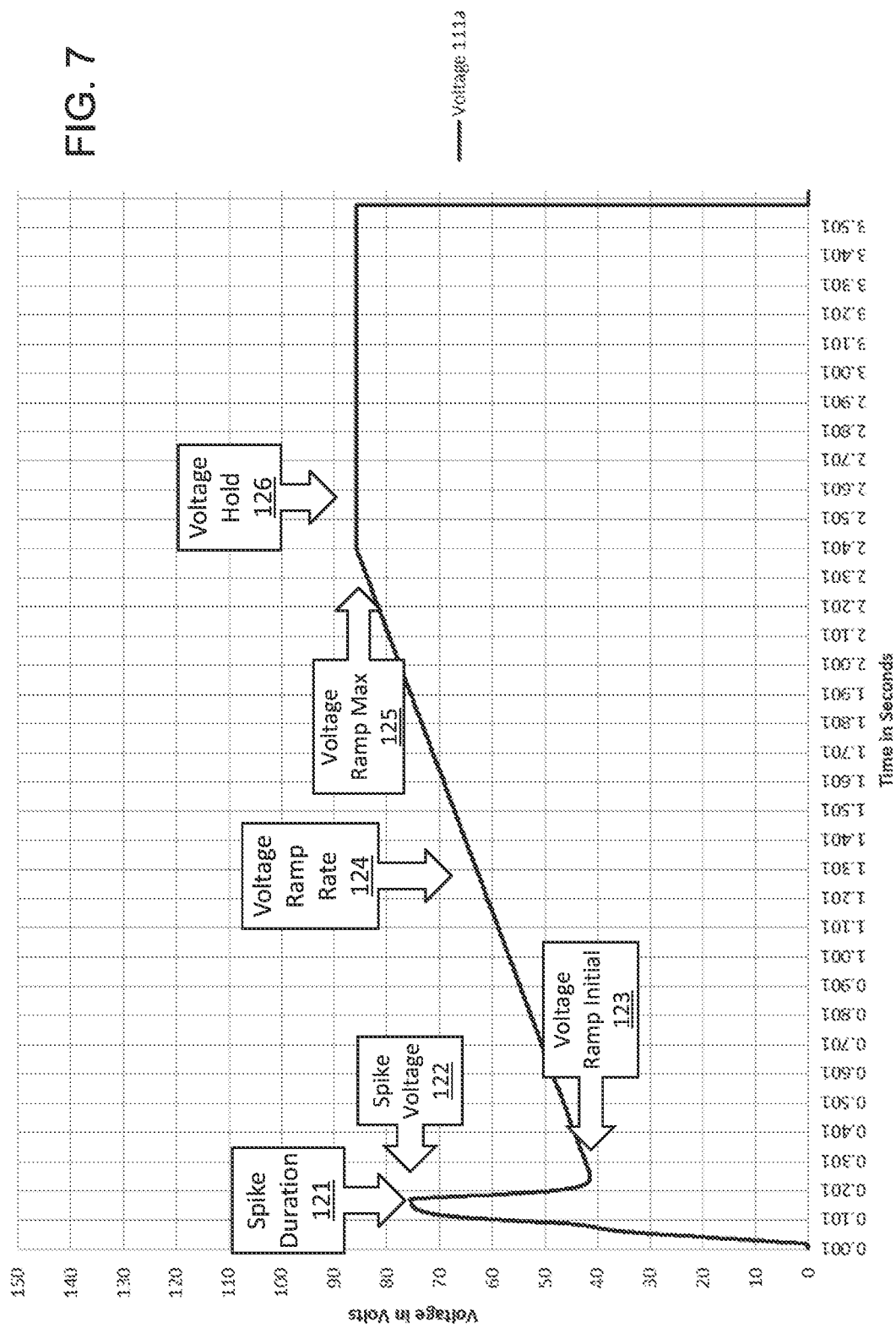
Figure 8:
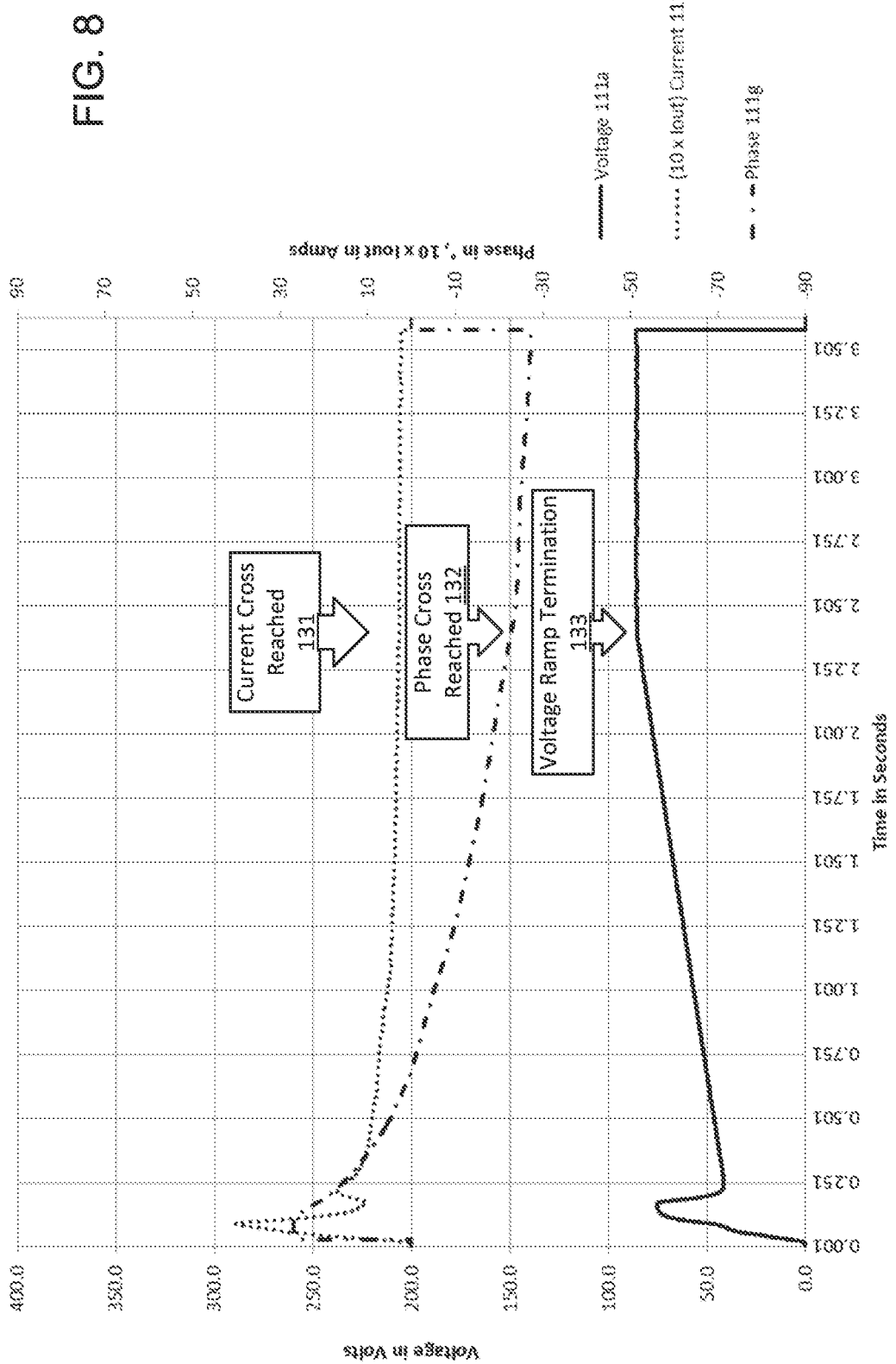
Figure 9:
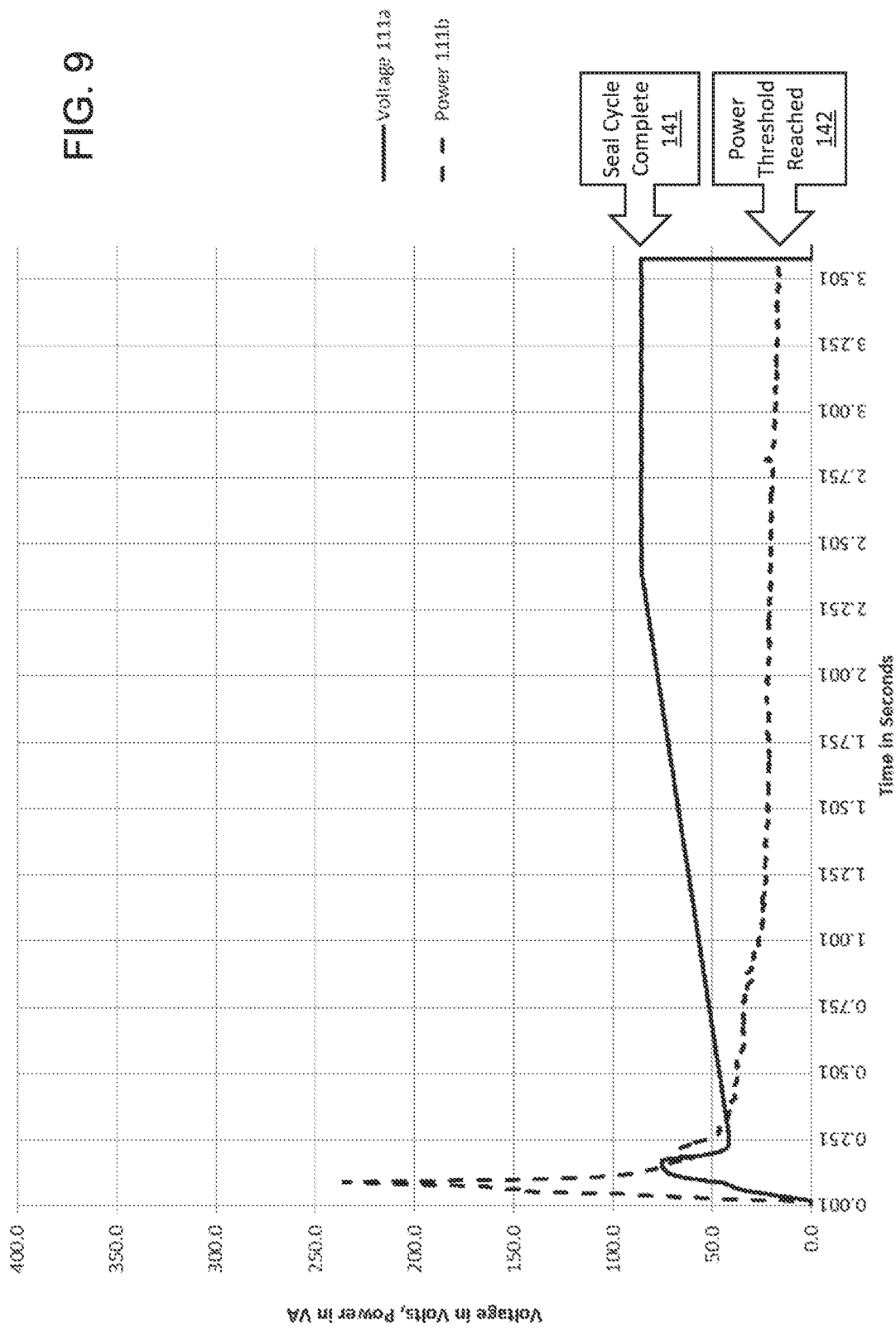

With reference to FIGS. 3-5, in accordance with various embodiments, a bipolar electrosurgical instrument 20 is provided. In the illustrated embodiment, the instrument 20 includes an actuator 24 coupled to an elongate rotatable shaft 26. The elongate shaft 26 has a proximal end and a distal end defining a central longitudinal axis therebetween. At the distal end of the shaft 26 are jaws 22 and at the proximal end is the actuator. In one embodiment, the actuator is a pistol-grip like handle.

The actuator 24 includes a movable handle 23 and a stationary handle or housing 28 with the movable handle 23 coupled and movable relative to the stationary housing. In accordance with various embodiments, the movable handle 23 is slidably and pivotally coupled to the stationary housing. In operation, the movable handle 23 is manipulated by a user, e.g., a surgeon to actuate the jaws, for example, selectively opening and closing the jaws.

In accordance with various embodiments, the actuator 24 includes a latch mechanism to maintain the movable handle 23 in a second position with respect to the stationary housing 28. In various embodiments, the movable handle comprises a latch arm which engages a matching latch contained within stationary handle for holding the movable handle at a second or closed position. The actuator in various embodiments also comprises a wire harness that includes insulated individual electrical wires or leads contained within a single sheath. The wire harness can exit the stationary housing at a lower surface thereof and form part of the cabled connection. The wires within the harness can provide electrical communication between the instrument and the electrosurgical generator and/or accessories thereof.

In various embodiments, a switch is connected to a user manipulated activation button 29 and is activated when the activation button is depressed. In one aspect, once activated, the switch completes a circuit by electrically coupling at least two leads together. As such, an electrical path is then established from an electrosurgical generator to the actuator to supply RF energy. In various embodiments, the instrument comprises a translatable mechanical cutting blade that can be coupled to a blade actuator such as a blade lever or trigger 25 of the actuator. The mechanical cutting blade is actuated by the blade trigger 25 to divide the tissue between the jaws.

In one embodiment, the actuator includes a rotation shaft assembly including a rotation knob 27 which is disposed on an outer cover tube of the elongate shaft 26. The rotation knob allows a surgeon to rotate the shaft of the device while gripping the actuator 24. In accordance with various embodiments, the elongate shaft 26 comprises an actuation tube coupling the jaws 22 with the actuator.

Attached to the distal end of the elongate shaft are jaws 22 that comprise a first jaw 31 and a second jaw 33. In one embodiment, a jaw pivot pin pivotally couples the first and second jaws and allows the first jaw to be movable and pivot relative to the second jaw. In various embodiments, one jaw is fixed with respect to the elongate shaft such that the opposing jaw pivots with respect to the fixed jaw between an open and a closed position. In other embodiments, both jaws can be pivotally coupled to the elongate shaft such that both jaws can pivot with respect to each other.

The first or upper jaw 31 includes an electrode plate or pad. Similarly, the second or lower jaw 33 includes an electrode. The electrode of the upper jaw 31 and the electrode of the lower jaw 33 are electrically coupled to the electrosurgical generator 10 via wires and connectors to supply RF energy to tissue grasped between the electrodes. The electrodes, as such, are arranged to have opposing polarity and to transmit RF energy therebetween. The upper jaw in various embodiments also includes an upper jaw support with an assembly spacer positioned between the upper jaw support and the electrode. The upper jaw also includes an overmold or is overmolded. The lower jaw includes a lower jaw support and the electrode. In the illustrated embodiment, the electrode is integrated or incorporated in the lower jaw support and thus the lower jaw support and the electrode form a monolithic structure and electrical connection. A blade channel extends longitudinally along the length of the upper jaw, the lower jaw or both through which the blade operationally traverses. Surrounding a portion of the blade channel are one or more conductive posts. The conductive posts assist in strengthening the blade channel and support the tissue to be cut. The conductive posts also assist in ensuring the tissue being cut adjacent or proximate to the blade channel is fused as the conductive posts also participate in the transmission of RF energy to the tissue grasped between the jaws. The lower jaw also includes an overmold or is overmolded.

In accordance with various embodiments, the electrodes have a generally planar sealing surface arranged to atraumatically contact and compress tissue captured between the jaws. The sealing surface in various embodiments include outcroppings (e.g., four outcroppings) uniformly spaced along the length of the jaw with branches disposed between the outcroppings. As such, the overall footprint of the sealing surface or area is reduced thereby increasing current density applied to the tissue and decreasing the current requirements for the supply of RF energy as a whole. Sealing of the tissue is thus enhanced causing high burst pressure averages in both in vivo and ex vivo conditions.

The electrode sealing surface also provides cutouts or spaces 34, 35 between the sealing surface and the edges of the jaws and between outcroppings to allow tissue room to shrink or move and reduces tissue stress due to the shrinkage or contraction of the tissue during the sealing cycle and stress caused by compression of tissue at the edges of the jaws. Similarly, the gradual spacing removes current density peaks at the edges of the electrode.

In various embodiments, the outcroppings keep the seal width 32 consistent while leaving room for the conductive posts in which a consistent seal width of the seal surface limits the total seal surface area. In various embodiments, the upper jaw includes an outer seal surface profile that matches the lower jaw profile preventing non-linear current transfer through the tissue. The upper jaw, as such, in various embodiments, includes outcroppings to match the outcroppings of the lower jaw. Also, additional area at the outcroppings of the upper jaw enhances localized strength of a conductive stop landing surface. Also, the outcroppings of the upper jaw provides a landing surface or area 37 for the interaction of the conductive posts of the lower jaws that enhances localized strength of the landing area. In various embodiments, the outcroppings are conductive and include a sealing or inner surface through which tissue been the jaws are compressed and RF energy is supplied to the tissue between the jaws.

The electrodes of the upper and lower jaws in various embodiments have a seal surface in which the width of the seal surface is uniform and follows along the pattern of the plurality of outcroppings. As such, the seal surface has elongate portions with curved portions spaced between the elongate portions and the width of the seal surface is uniform, constant or remains unchanged throughout. The seal surface of the upper and lower jaws are minimized and as such has a reduced surface area relative to the overall surface area capable of be formed for the given overall dimensions of the jaw.

In various embodiments, the sealing surface of at least one of the jaws includes a blade pocket or cutout that is arranged to collect and/or clear eschar, debris or coagulated blood. As such, the blade being locked, misaligned or prevented or restricted in returning is avoided and thereby enhancing the return of the blade back to its initial or precut position. In various embodiments, one or more blade pockets or cutouts 36, 39 are disposed at a distal end of the sealing surface and in various embodiments extend from a distal end of the blade channel. In various embodiments, the blade pocket is an enlarged bulbous opening at the end of the blade channel being elongate and uniform. As such, the blade pocket eases blade actuation and ensures automatic blade retraction when eschar builds up on the seal surface and in blade channel of the jaws. The distal blade pocket on both upper and lower jaws in various embodiments provide accumulated eschar to be pushed forward and out of the blade channel. The pocket also allows new eschar to push out older eschar build up out of the jaws to ease cleaning or more effective cleaning of the instrument.

In various embodiments, the jaws are curved to increase visualization and mobility of the jaws at the targeted surgical site and during the surgical procedure. The jaws have a proximal elongate portion that is denoted or aligned with straight lines and a curved distal portion denoting or defining a curve that is connected to the straight lines. In various embodiments, the proximal most portion of the proximal elongate portion has or delimits a diameter that equals or does not exceed a maximum outer diameter of the jaws or elongate shaft. The jaws in various embodiments have a maximum outer diameter in which the proximal most portion of the jaw and the distal most portion of the jaws remains within the maximum outer diameter. The curved distal portion has or delimits a diameter that is smaller than the maximum outer diameter and the diameter of the proximal most portion of the proximal elongate portion. In various embodiments, the jaw has a deeper inner curve cut-out than the outer curve and in various embodiments the tip of the jaws are tapered for blunt dissection. The jaws include a blade channel having an proximal elongate channel curving to a distal curved channel in which the proximal elongate channel is parallel and offset to the longitudinal axis of the elongate shaft of the electrosurgical instrument. As such, visibility and mobility at the jaws are maintained or enhanced without increasing jaw dimensions that may further reduce the surgical working area or require larger access devices or incisions into the patient's body.

In some embodiments, electrode geometry of the conductive pads of the jaw assembly ensures that the sealing area or surface completely encloses the distal portion of the cutting path. In accordance with various embodiments, the dimensions of the jaw surfaces are such that it is appropriately proportioned with regards to the optimal pressure applied to the tissue between the jaws for the potential force the force mechanism can create. Its surface area is also electrically significant with regards to the surface area contacting the tissue. This proportion of the surface area and the thickness of the tissue have been optimized with respect to its relationship to the electrical relative properties of the tissue.

In various embodiments, the lower jaw 33 and an associated conductive pad have an upper outer surface arranged to be in contact with tissue. The upper surfaces are angled or sloped and mirror images of each other with such positioning or orientation facilitating focused current densities and securement of tissue. In various embodiments, the lower jaw is made of stainless steel and is as rigid as or more rigid than the conductive pad. In various embodiments, the lower jaw comprises rigid insulators made of a non-conductive material and are as rigid as or more rigid than the lower jaw or the conductive pad. In various embodiments, the lower jaw and the conductive pad are made of the same material.

In accordance with various embodiments, the RF energy control process, script or system to seal or fuse tissue is divided into one or more control sections. In the illustrated embodiments, the control process, script or system comprises four sections, a voltage spike, voltage reduction and ramp, a ramp termination and an RF end. In various embodiments, the control process, script or system comprises one or more sections in various combinations or orders thereof. If errors or an unexpected result from a section or between sections occur, the process terminates. In various embodiments, such errors comprises a short or open detection. In one embodiment, a short detection error is determined by the generator when a measured phase angle of the supplied RF energy by the generator equals or exceeds a predetermined value, e.g., sixty degrees. In one embodiment, an open detection error is determined by the generator when a measured current of the supplied RF energy equals or exceeds a predetermined value, e.g., 2 or 4 Amps. Completion of the control process without errors indicates a successful tissue seal. A successful tissue seal in accordance with various embodiments is recognized as the tissue seal being able to withstand a predetermined range of burst pressures or a specific threshold pressure.

In accordance with various embodiments, it has been identified that tissue seal formation is dependent on denaturization and cross linkage of the native collagen present in vasculature extra cellular matrix which starts at about 60° C. It was also identified that the strength of this matrix is highly dependent on desiccation of the seal site via vaporization of water present in the sealed tissue. Additionally, at a temperature of at least 80° C., bonds between the denatured collagen and other living tissues can be created. Furthermore, it was identified that collagen degrades in response to duration under elevated temperature rather than the peak temperature of exposure. As such, exposing tissue to high temperature conditions, e.g., 100° C., for the duration of a relatively short seal cycle does not impact the structure of the collagen but allows for vaporization of water. The total time to seal tissue, in accordance with various embodiments, is reliant on heating the structure to the high temperature, e.g., 100° C., to vaporize water such that the denatured collagen crosslinks and bonds to tissue and to limit collagen-water hydrogen bonding. To optimize seal time, it was therefore found to be desirable to achieve 100° C. within the grasped tissue as quickly as possible to begin the desiccation process.

As such, in accordance with various embodiments, after RF energy has been initiated and/or various device checks are performed, the generator employs through the supplied RF energy a high voltage spike or pulse. In various embodiment, the voltage potential of the RF energy applied to the tissue driven as a spike such that a high amount of power is applied at the start of the seal cycle in order to maximize energy transfer, and by proxy tissue temperature.

In accordance with various embodiments of the electrosurgical generator and removable instruments it was identified that while rapid heating is desirable to vaporize latent fluid as quickly as possible for seal time optimization, vaporization happening too quickly can cause the seal structure to fail as the extra vapor struggles to escape. Such identification in some instances may only be observed through burst pressure testing. Once the voltage spike is complete, the system reduces the voltage to a predetermined level and slowly ramps up the voltage of the supplied RF energy. While the ramp occurs, in various embodiments, sufficient power is being applied to the tissue to maintain a temperature sufficient for desiccation. This allows for continuous vaporization at a rate that does not cause seal structural failures and enhances vessel sealing performance.

In various embodiments, a high peak voltage provides a seal in a shorter amount of time due to higher energy transfer, however it has been shown experimentally that application of high voltage levels may cause the sealed tissue to adhere to the active electrodes. As such, it has been found that termination of the voltage ramp at a lower peak voltage and holding that voltage output constant at the end allows for continued energy application while reducing the potential for tissue adherence. Determination of when to terminate this ramp, in accordance with various embodiments, is conducted by monitoring the phase and current of the supplied RF energy. As the tissue desiccates, the phase will become more capacitive and will draw less current. By terminating the ramp at a fixed current value as it falls and when the phase is capacitive, the desiccation level of the tissue can be categorized. This variable voltage set point allows the seal cycle to adjust the energy application based on electrical and structural differences in tissues being sealed.

In various embodiments, in order to achieve the appropriate temperature of the tissue to cause the associated tissue effect, the phase angle, current and/or power of the applied RF energy are measured, calculated and/or monitored. FIGS. 6-9 provide a graphical representation of an exemplary seal cycle in accordance with various embodiments. As illustrated, voltage 111a is shown relative to other RF output readings or indicators such as power 111b, impedance 111c, energy 111d, current 111f and phase 111g. Additionally, although shown in FIGS. 6-9, in various embodiments, the generator is configured to not measure or calculate one or more of the indicators or readings, e.g., temperature, to reduce operational and power costs and consumptions and/or the number of parts of the generator. The additional information or readings are generally provided or shown for contextual purposes. Additionally, in various embodiments, impedance or temperature readings are not used or measured being imprecise or impractical.

As shown, the voltage of the RF energy 111a is increased to a high point in the seal cycle in the initial moments of the seal cycle and for a period relatively short compared to the total seal time to generate the voltage spike of RF energy 121, 122. During this voltage spike or pulse, energy transfer is maximized, exemplified by the power 111b and current 111f of the applied RF energy increasing to their highest points in the seal cycle. Subsequently, the voltage of the RF energy 111a is reduced 123 and ramped up 124,125, slowly, relative to the voltage spike. In various embodiments, the slow voltage ramp by the system seeks to maintain the tissue between the jaws close to 100 degrees C. and thereby control the boiling rate of water in the tissue. In accordance with various embodiments, in order to achieve the appropriate tissue effect of sealing the tissue, the phase angle, current and power of the applied RF energy are monitored. The phase angle of the applied RF energy crossing zero or becoming negative and/or the current being less than 60% the applicable current, e.g., less than 3000 mA, indicates that tissue between the jaws have become more capacitive and thereby drawing less current as water boils or otherwise vaporizes from the tissue being sealed 131, 132. Voltage of the RF energy is then held constant 126, 133 to reduce the potential for tissue adherence. At seal completion 141, e.g., within a predetermined time frame or period according to the system, RF energy supplied by the system is terminated or RF energy supply halted, disrupted or stopped. In various embodiments, the system determines the completion of the seal when the power of the supplied RF energy fails below a predetermined power threshold 142, such as 4% of the maximum power or 15 volt-amperes. In various embodiments, the ramp of RF energy is terminated and after a predefined time period according to the system, RF energy supplied by the system is terminated or RF energy supply halted, disrupted or stopped.

In various embodiments, the time period in which the generator generates the voltage spike of RF energy is smaller than the overall seal cycle and/or the time period in which the generator causes the voltage of the RF energy to be reduced and ramped up slowly. In various embodiments, the time period in which the generator holds the voltage of the RF energy constant, is smaller than the overall seal cycle and/or greater than the time period in which the generator generates the voltage spike of RF energy.

In various embodiments, the system identifies unintended current draw provided for example in some tissue bundles that draw the maximum current or power that can be supplied by the generator. While the system is under such a current condition, the supply of RF energy required to seal the tissue may not be sufficient or be efficiently supplied by the system. In various embodiments, to handle such a condition, the system determines if the current of the RF energy output is greater than 95% the allowable maximum current, e.g., 4750 mA. If so, the system waits or delays further to ensure that the current has sufficiently dropped indicating that sufficient desiccation of the tissue has occurred. If after such a delay the current has not sufficiently dropped, an error is indicated and/or RF energy being supplied is halted. In accordance with various embodiments, the system determines or confirms that the current has sufficiently dropped if the current falls below 90% of the maximum, e.g., 4500 mA. As such, the system determines that the current condition has ceased and/or the tissue has started boiling.

Figure 10:
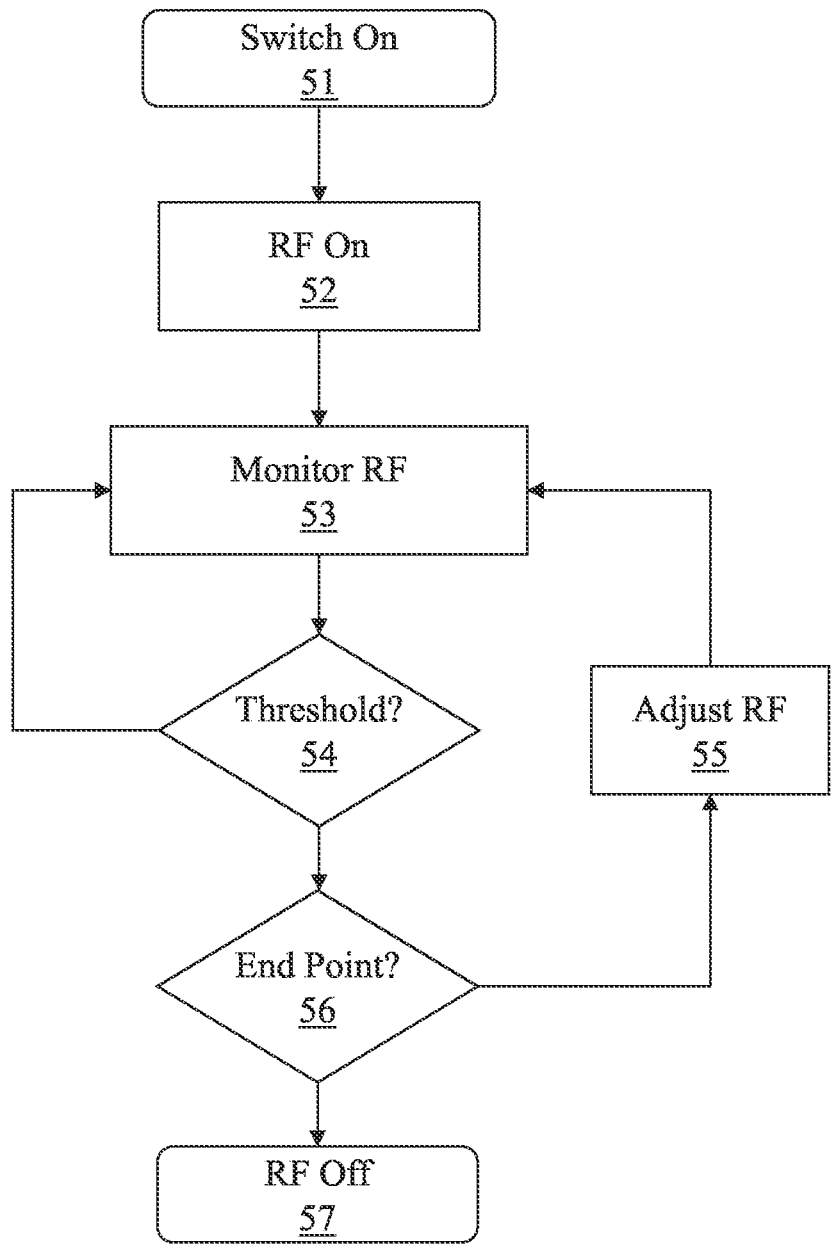
FIG. 10 is a flow chart illustrating operations of an electrosurgical system in accordance with various embodiments of the present invention.

In one embodiment, as illustrated in FIG. 10, an electrosurgical process such as a tissue fusion or sealing process starts with depressing a switch or moving an actuator on the tool (51), which based on a positive result of initial checks, the generator supplies RF energy having a predetermined voltage from the generator to the electrosurgical tool and ultimately to the tissue (52). After RF power is turned on and is being supplied continuously by the generator, the generator monitors the supplied RF energy (53). At or upon a predefined or predetermined point, condition or threshold (54) being reached or exceeded, voltage of the supply of RF energy and the predefined point are adjusted or newly selected (55) and the generator continues to monitor the supplied RF energy (52). Should the predefined condition mark the end of the fusion or seal cycle, e.g., tissue seal is complete, and such a condition is reached or exceeded, the generator terminates or halts the supply of RF energy (57). In various embodiments, an acoustical and/or visual signal is provided indicating that the tissue is fused or sealed (or that an error has occurred (e.g., shorting of the electrodes) and/or an unexpected condition has occurred (e.g., permissible although unexpected switch release)). In accordance with various embodiments, the predefined point, condition or threshold and/or initialization checks are determined based on a tool algorithm or script provided for a connected electrosurgical tool, procedure or preference.

Figure 11:
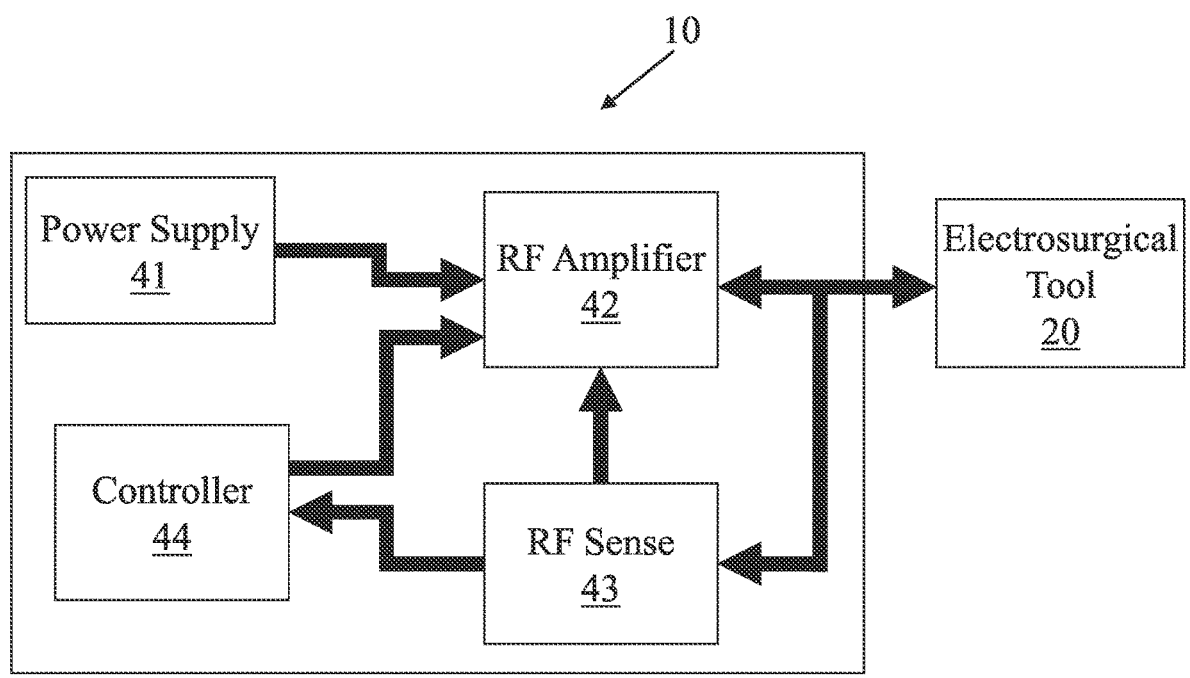
FIG. 11 is a schematic block diagram of portions of an electrosurgical system in accordance with various embodiments of the present invention.

Referring now to FIG. 11, in one embodiment, the electrosurgical generator 10 is connected to AC main input and a power supply 41 converts the AC voltage from the AC main input to DC voltages for powering various circuitry of the generator. The power supply also supplies DC voltage to an RF amplifier 42 that generates RF energy. In one embodiment, the RF amplifier 42 converts 100 VDC from the power supply to a sinusoidal waveform with a frequency of 350 kHz which is delivered through a connected electrosurgical instrument. RF sense circuitry 43 measures/calculates voltage, current, power and phase at the output of the generator in which RF energy is supplied to a connected electrosurgical instrument 20. The measured/calculated information is supplied to a controller 44.

In one embodiment, the RF sense analyzes the measured AC voltage and current from the RF amplifier and generates DC signals for control signals including voltage, current, power, and phase that are sent to the controller for further processing. In one embodiment, RF sense 43 measures the output voltage and current and calculates the root means square (RMS) of the voltage and current, apparent power of the RF output energy and the phase angle between the voltage and current of the RF energy being supplied through a connected electrosurgical instrument. In particular, the voltage and current of the output RF energy are processed by analog circuitry of the RF sense to generate real and imaginary components of both voltage and current. These signals are processed by an field-programmable gate array (FPGA) to give different measurements relating to voltage and current, including the RMS measurements of the AC signals, phase shift between voltage and current, and power. Accordingly, in one embodiment, the output voltage and current are measured in analog, converted to digital, processed by an FPGA to calculate RMS voltage and current, apparent power and phase angle between voltage and current, and then are converted back to analog for the controller.

In one embodiment, controller 44 controls or signals the RF amplifier 42 to affect the output RF energy. For example, the controller utilizes the information provided by the RF sense 43 to determine if RF energy should be outputted, adjusted or terminated. In one embodiment, the controller determines if or when a predetermined current, power and/or phase threshold has been reached or exceeded to determine when to terminate the output of RF energy. In various embodiments, the controller performs a fusion or sealing process described in greater detail herein and in some embodiments the controller receives the instructions and settings or script data to perform the sealing process from data transmitted from the electrosurgical instrument. As such, in various embodiments, the controller causes or adjusts the voltage of the RF energy being supplied by the RF Amplifier starting, holding and/or ending at predefined voltages and/or over predetermined time periods and/or based predetermined thresholds.

The RF Amplifier 42 generates high power RF energy to be passed through a connected electrosurgical instrument and in one example, an electrosurgical instrument for fusing or sealing tissue. In various embodiments, the RF Amplifier supplies RF energy to or through the electrosurgical instrument starting at a predefined first voltage and increasing to a predefined second voltage within a predetermined first time period. The RF Amplifier in accordance with various embodiments is configured to convert a 100 VDC power source to a high power sinusoidal waveform with a frequency of 350 kHz which is delivered to the connected electrosurgical device. The RF Sense 43 interprets the measured AC voltage and current from the RF amplifier 42 and generates DC control signals, including voltage, current, power, and phase, that is interpreted by the controller 44.

The generator including the controller and/or RF sense monitors and/or measures the RF energy being supplied is as expected. In various embodiments, the system, e.g., the controller and/or RF sense, monitors the voltage and/or current of the RF energy to ensure the voltage and the current are above predefined threshold values. The system, e.g., the controller and/or RF sense, also monitors, measures and/or calculates the phase and/or power of the supplied RF energy. The system, e.g., the controller and/or RF sense, ensures that the voltage, current, phase and/or power of the supplied RF energy is within an predefined voltage, current, phase and/or power window or range. In one embodiment, the voltage, current, phase and/or power window are respectively delimited by a predefined maximum voltage, current, phase and/or power and a predefined minimum voltage, current, phase and/or power. If the voltage, current, phase and/or power of the RF energy moves out of its respective window, an error is indicated. In one embodiment, the respective window slides or is adjusted by the system as RF energy is being supplied to seal the tissue between the jaws of the instrument. The adjustment of the respective window is to ensure that supplied RF energy is as expected. The system in various embodiments monitors the phase and/or current or rate of phase and/or current of the supplied RF energy to determine if the phase and/or current has reached or crossed a predefined phase and/or current threshold and if phase and/or current crossing has occurred, RF energy is supplied for a predefined time period before terminating.

In accordance with various embodiments, an operations engine of controller 44 enables the generator to be configurable to accommodate different operational scenarios including but not limited to different and numerous electrosurgical tools, surgical procedures and preferences. The operations engine receives and interprets data from an external source to specifically configure operation of the generator based on the received data.

The operations engine receives configuration data from a database script file that is read from a memory device of the electrosurgical instrument. The script defines the state logic used by the generator. Based on the state determined and measurements made by the generator, the script can define or set output levels as well as shutoff criteria. The script, in one embodiment, includes trigger events that include indications of a short condition, for example, when a measured phase is greater than 60 degrees, or an open condition, for example, when a measured current is less than 2 Amps.

Figure 12:
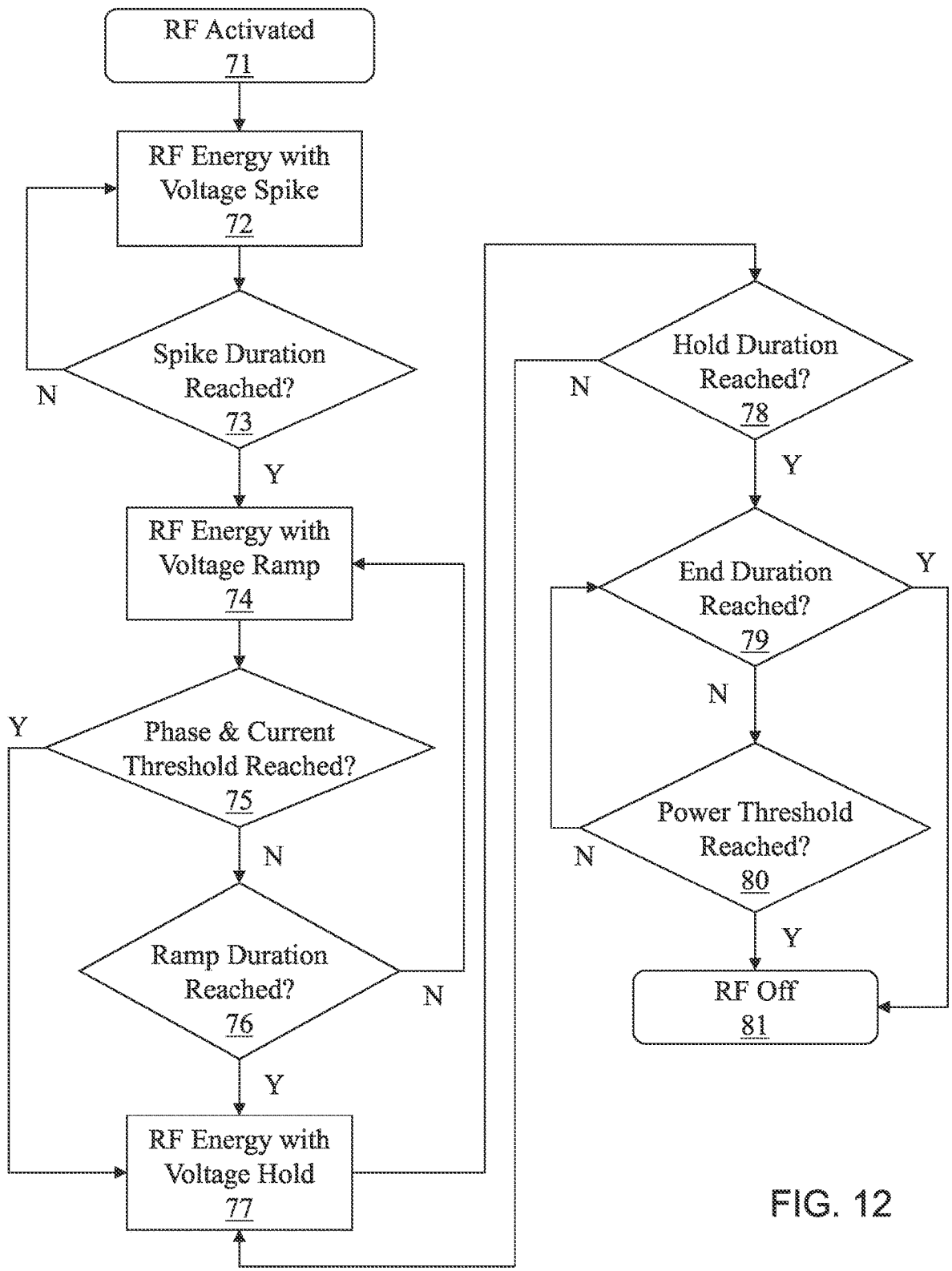
FIG. 12 is a flow chart illustrating operations of an electrosurgical system in accordance with various embodiments of the present invention.

Exemplary RF energy control process, script or system for the electrosurgical generator and associated electrosurgical tools for fusing or sealing tissue in accordance with various embodiments are shown in FIG. 12. In various embodiments, as illustrated in FIG. 12, for example, RF energy is supplied by the generator through the connected electrosurgical tool (71) in which the generator sets the voltage of the supplied RF energy to generate the RF energy to have a voltage spike (72). The generator monitors or waits a predefined time period or spike duration (73) while continuing to supply RF energy (72). Once the spike duration 121 has expired or passed, the generator adjusts the voltage of the supplied RF energy to a predefined minimum value 123 and the generator causes the voltage of the RF energy to gradually ramp or increase 124 to a predefined voltage level 125 (74). The generator also monitors at least the phase, voltage, current, power and/or change/rate thereof of the supplied RF energy (75). If a phase and current condition is reached or equals, exceeds or falls below a predetermined threshold or value (75), voltage is held constant 126 and/or the ramp terminated 133 (77). In various embodiments, if a phase condition or threshold is reached or falls below a predetermined phase threshold value 132 and/or a current condition or value is reached or falls below a predetermined current threshold value 131 (75), the generator adjusts the voltage of the supplied RF energy to be constant (77). If the phase and current condition or threshold is not reached or crossed, the generator monitors or waits a predefined time period or ramp duration (76) while continuing to supply RF energy (74) and monitoring the phase and current conditions (75). If the ramp duration has expired or passed, the generator adjusts the voltage of the supplied RF energy to be constant (77). With the RF energy being held constant, the generator monitors or waits a predefined time period or hold duration (78) while continuing to supply RF energy (77). Once the hold duration has expired or passed, the monitors or waits a predefined time period or end duration (79) while continuing to supply RF energy. If the end duration has expired or passed, the process is done or termination procedures are initiated and/or RF energy supplied by the generator is stopped (81). If the end duration has not expired or passed, the generator determines if a power condition or threshold is reached or falls below a predetermined power threshold or value 142 (80). If the power condition or threshold is reached or crossed, the process is done or termination procedures are initiated and/or RF energy supplied by the generator is stopped (81). If the power condition or threshold is not reached or crossed, the generator continues to supply RF energy, while monitoring the power condition and end duration time period.

In various embodiments, prior to the start of the process, impedance is measured to determine a short or open condition through a low voltage measurement signal delivered to a connected electrosurgical tool. In one embodiment, passive impedance is measured to determine if the tissue grasped is within the operating range of the electrosurgical tool (2-200Ω). If the initial impedance check is passed, RF energy is supplied to the electrosurgical tool. After which impedance/resistance is not measured or ignored.

In various embodiments, voltage of the RF energy is applied in a ramping fashion (74) starting from 35-45% to at most 65-100% of a global voltage setting or, in one embodiment, an user selected level. In various embodiments, the voltage of the RF energy is applied in a ramping fashion starting from 35-40 volts, e.g., a predefined third voltage, to 65-90 volts, e.g., a predefined fourth voltage, over 1.5-4 seconds, e.g., a predetermined second time period. In various embodiments, the voltage is held constant at a voltage, smaller than and/or equal to the at a predefined voltage equal and/or below the end of the ramp voltage, e.g., the predefined fourth voltage, and/or for a predetermined time period. In various embodiments, this time period is greater than time periods for the voltage spike and/or the time period determined for the voltage ramp. In various embodiments, voltage of the RF energy is applied as a voltage spike (72) starting from 30-40% to at most 75-100% of a global voltage setting or, in one embodiment, an user selected level. In various embodiments, the voltage of the RF energy is applied in as a voltage spike starting from 35-40 volts, e.g., a predefined first voltage, to 75-90 volts, e.g., a predefined second voltage, over 50-300 ms seconds, e.g., a predetermined first time period.

In accordance with various embodiments, phase is monitored in conjunction with current for open and short events while RF energy is being applied and in one embodiment after phase and/or change of phase stop or endpoints is reached to evaluate or determine if a false indication of fusion (caused by an open or short) has been reached.

In accordance with various embodiments, the generator is configured to provide additional regulation of various parameters or functions related to the output of the RF energy, voltage, current, power and/or phase and the operations engine is configured to utilize the various parameters or functions to adjust the output of RF energy. In one exemplary embodiment, the control circuitry provides additional regulation controls for direct regulation of phase in which voltage, current and/or power output would be adjusted to satisfy specified phase regulation set points provided by the operations engine.

In accordance with various embodiments, the generator utilizes the monitored, measured and/or calculated values of voltage, power, current and/or phase, e.g., control indicators, to recognize and act or perform operation conditions. In various embodiments, additional measurements or calculations based on the measured values related to RF output regulation circuitry are provided by the script or operations engine to recognize and act upon additional or different events related to or trigger by the additional measurements or calculations relative to other measurements or thresholds.

The additional measurements in one embodiment include error signals in combination with a pulse width modulation (PWM) duty cycle used to regulate the output of voltage, current and/or power or other similar regulation parameters. Different or additional events or indicators that could be identified and triggered in various embodiments could be transitions from one regulation control to another regulation control (e.g. current regulation to power regulation). In various embodiments, subsequent impedance or temperature checks or measurements are not performed being imprecise and/or impractical.

In various embodiments, the generator utilizes many states, control points or checks to identify a phase, current or power value and respectively for a positive or negative trend. An error is signaled if the generator does not identify an expected trend. The multistate checks increase or enhance the generator resolution in identifying an expected RF output trend over different types of tissue.

In various embodiments, the generator also monitors the phase or current and/or rate of phase or current to determine if the connected electrosurgical tool has experienced an electrical open or short condition. In one example, the generator identifies an electrical short condition of the connected electrosurgical instrument by monitoring the phase of the applied or supplied RF energy and if the monitored phase is greater than a predefined maximum phase value, an electrical short condition is identified. Similarly, in one example, the generator identifies an electrical open condition of the connected electrosurgical instrument by monitoring the current of the applied or supplied RF energy and if the monitored current is less than a predefined minimum current, an electrical open condition is identified. In either or both cases, the generator upon discovery of the open and/or short conditions indicates an error and RF energy being supplied is halted.

In various embodiments, the predefined process as described throughout the application is loaded into a memory module embedded into a connector removably connected to a plug and/or cable connection to an electrosurgical instrument. In various embodiments, the device script or process is programmed onto an adapter PCBA contained within the device connector or hardwired into circuitry within the device connector during manufacture/assembly. The script source file is written in a custom text-based language and is then compiled by a script compiler into a script database file that is only readable by the generator. The script file contains parameters specifically chosen to configure the generator to output a specific voltage (e.g., 100 v (RMS)), current (e.g., 5000 mA (RMS)), and power level (e.g., 300 VA). In various embodiments, a device key programmer device reads and then programs the script database file into the memory of the adapter PCBA.

Turning now to some of the operational aspects of the electrosurgical tool or instrument described herein in accordance with various embodiments, once a vessel or tissue bundle has been identified for fusing, the first and second jaws 31, 33 are placed around the tissue. The handle 21 is squeezed and thereby pivots the jaws together to effectively grasp the tissue. The actuator has a first or initial position in which the jaws 22 are in an open position with the handle 23 positioned away or spaced from the housing 28.

The depression of the fuse button 29 by the surgeon causes the application of the radio frequency energy to the tissue between the jaws. Once the tissue has been fused, the actuator can be reopened by the handle being released and moved away from stationary housing 28. To cut tissue between the jaws, the user can actuate the blade trigger 25.

When the blade trigger is moved proximally, a cutting blade moves distally to divide the tissue between the jaws. When the surgeon releases the blade trigger, the blade spring resets the cutting blade to its original position. In accordance with various embodiments, the actuator has a cut position in which the jaws 22 are in a closed position, the movable handle is closed and latched and the blade trigger has been depressed advancing the cutting blade to its distal most position.

In various embodiments, an intermediate or unlatched position is provided in which the jaws are in a closed or proximate position but the handle is unlatched. As such, if the handle is released, the handle will return to its original or initial position. In one embodiment, the blade trigger may not be activated to cut tissue between the jaws but the fuse button or switch may be activated to fuse tissue between the jaws. In various embodiments, a latched position is provided in which the jaws are in a closed or proximate position and the handle is latched. As such, if the handle is released, the handle will not return to its original or initial position. In one embodiment, the fuse button or switch may be activated to fuse tissue between the closed jaws and/or the blade trigger may be activated to cut tissue between the jaws.

As described, in accordance with various embodiments, the electrosurgical instrument has a first (open) state in which the jaws are spaced from each other and thus the handle is also spaced from the stationary housing. The instrument is thus positioned to grasp tissue between the jaws. In the second (intermediate) state of the instrument, the jaws are proximate to each other to grasp tissue between the jaws and likewise the handle and housing are proximate to each other. The surgeon can revert back to the first state by opening the jaws and thus positioning the jaws again to grasp the tissue or other tissue. In the third (closed) state of the instrument, the handle is moved further closer to the stationary housing and latches to the stationary housing. Movement to the third state, tissue grasped between the jaws can be cut through the activation of the blade lever. Movement to the third state, in which the handle is latched to the housing, reduces the potential of unintentionally releasing the tissue. Also, inadvertent cutting of tissue or along the wrong tissue lines are avoided. Additionally, this state allows the application of constant and continuous predefined compression or range of compression on the tissue between the jaws before, during and after the activation of the RF energy, thereby enhancing the sealing or fusion of the tissue between the jaws. In accordance with various embodiments, application of RF energy can occur once the handle and jaws are in at least the second state and once the fuse button is activated by the surgeon.

It is noted that in various embodiments to avoid false readings, the electrosurgical generator does not measure resistance or impedance of the tissue during the supply of RF energy to the tissue. In accordance with various embodiments, an electrosurgical system is provided that decreases thermal spread and provides efficient power delivery for sealing vessels or tissue in contact with a bipolar electrosurgical instrument through the controlled and efficient supply of RF energy.

As described throughout the application, the electrosurgical generator ultimately supplies RF energy to a connected electrosurgical instrument. The electrosurgical generator ensures that the supplied RF energy does not exceed specified parameters and detects faults or error conditions. In various embodiments, an electrosurgical instrument provides the commands or logic used to appropriately apply RF energy for a surgical procedure. An electrosurgical instrument for example includes memory having commands and parameters that dictate the operation of the instrument in conjunction with the electrosurgical generator. For example, in a simple case, the generator can supply the RF energy but the connected instrument decides how much or how long energy is applied. The generator, however, does not allow the supply of RF energy to exceed a set threshold even if directed to by the connected instrument thereby providing a check or assurance against a faulty instrument command.

As described generally above and described in further detail below, various electrosurgical instruments, tools or devices can be used in the electrosurgical systems described herein. For example, electrosurgical graspers, scissors, tweezers, probes, needles, and other instruments incorporating one, some, or all of the aspects discussed herein can provide various advantages in an electrosurgical system. Various electrosurgical instruments and generator embodiments and combinations thereof are discussed throughout the application. It is contemplated that one, some, or all of the features discussed generally throughout the application can be included in any of the embodiments of the instruments, generators and combinations thereof discussed herein. For example, it can be desirable that each of the instruments described include a memory for interaction with the generator as previously described and vice versa. However, in other embodiments, the instruments and/or generators described can be configured to interact with a standard bipolar radio frequency power source without interaction of an instrument memory. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Likewise, such software components may be interchanged with hardware components or a combination thereof and vice versa.

Further examples of the electrosurgical unit, instruments and connections there between and operations and/or functionalities thereof are described in U.S. patent application Ser. No. 12/416,668, filed Apr. 1, 2009, entitled "Electrosurgical System"; Ser. No. 12/416,751, filed Apr. 1, 2009, entitled "Electrosurgical System"; Ser. No. 12/416,695, filed Apr. 1, 2009, entitled "Electrosurgical System"; Ser. No. 12/416,765, filed Apr. 1, 2009, entitled "Electrosurgical System"; and Ser. No. 12/416,128, filed Mar. 31, 2009, entitled "Electrosurgical System"; the entire disclosures of which are hereby incorporated by reference as if set in full herein. Certain aspects of these electrosurgical generators, tools and systems are discussed herein, and additional details and examples with respect to various embodiments are described in U.S. Provisional Application Nos. 61/994,215, filed May 16, 2014, entitled "Electrosurgical Fusion Device"; 61/944,185, filed May 16, 2014, "Electrosurgical Generator with Synchronous Detector"; 61/994,415, filed May 16, 2014, "Electrosurgical System"; and 61/944,192, filed May 16, 2014, entitled "Electrosurgical Generator", the entire disclosures of which are hereby incorporated by reference as if set in full herein.

The above description is provided to enable any person skilled in the art to make and use the surgical devices and perform the methods described herein and sets forth the best modes contemplated by the inventors of carrying out their inventions. Various modifications, however, will remain apparent to those skilled in the art. It is contemplated that these modifications are within the scope of the present disclosure. Additionally, different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth. Also, embodiments of the present invention should be considered in all respects as illustrative and not restrictive.

The invention claimed is:

1. An electrosurgical system comprising:
    an electrosurgical instrument; and
    an electrosurgical generator removably coupled to the electrosurgical instrument, the electrosurgical generator configured to:
        supply RF energy having an initial voltage spike to the electrosurgical instrument, wherein the initial voltage spike has a voltage increasing between a first predetermined voltage level to a second predetermined voltage level,
        change voltage of the supplied RF energy from the second predetermined voltage level to a third predetermined voltage level with a following voltage ramp up to a fourth predetermined voltage level, wherein the third predetermined voltage level is less than the second predetermined voltage level,
        monitor current of the supplied RF energy during the following voltage ramp,
        terminate the following ramp up and hold the voltage of the supplied RF energy at a post-ramp voltage level when the monitored current drops below a pre-determined current threshold, and
        end the supply of the RF energy to the electrosurgical instrument after holding the voltage of the supplied RF energy at the post-ramp voltage level for a pre-determined period of time.

2. The electrosurgical system of claim 1, wherein the electrosurgical generator is configured to further monitor for one or more error conditions, wherein detection of one of the one or more error conditions causes the supply of RF energy to the electrosurgical instrument to be terminated.

3. The electrosurgical system of claim 2, wherein the one or more error conditions comprise:
    a short circuit corresponding to a measured phase of the supplied RF energy equaling or exceeding a pre-determined threshold, or
    an open circuit corresponding to the monitored current of the supplied RF energy equaling or exceeding a pre-determined threshold.

4. The electrosurgical system of claim 2, wherein the one or more error conditions comprise an unintended current draw corresponding to the monitored current being greater than a pre-determined threshold for a fixed period of time.

5. The electrosurgical system of claim 4, wherein the unintended draw error corresponds to the monitored current being greater than 95% of an allowable maximum current.

6. The electrosurgical system of claim 1, wherein the electrosurgical generator further monitors phase of the supplied RF energy during the following voltage ramp.

7. The electrosurgical system of claim 6, wherein the electrosurgical generator further terminates the following ramp up when the monitored current drops below the pre-determined current threshold and the monitored phase is capacitive.

8. The electrosurgical system of claim 1, wherein the electrosurgical generator further monitors a power level of the supplied RF energy.

9. The electrosurgical system of claim 8, wherein the electrosurgical generator ends the supply of RF energy to the electrosurgical instrument when the monitored power level falls below a pre-determined power threshold while the voltage of the supplied RF energy at the post-ramp voltage level is being held for a pre-determined period of time.

10. The electrosurgical system of claim 9, wherein the pre-determined power threshold is 4% of a maximum allowable power.

11. An electrosurgical generator comprising:
an RF amplifier configured to supply RF energy to be passed through to a connected electrosurgical instrument;
an RF sense circuitry configured to generate information for a controller, wherein the generated information comprises measurements of output voltage and output current of the supplied RF energy; and
the controller determines that at least one of the generated information from the RF sense circuitry meets or exceeds one or more pre-determined thresholds and subsequently signals the RF amplifier to modify the supplied RF energy based on the determination,
wherein the controller signals the RF amplifier to modify the supplied RF energy to:
supply RF energy with an initial voltage spike to the electrosurgical instrument, wherein the initial voltage spike has a voltage increasing between a first predetermined voltage level to a second predetermined voltage level,
change the voltage of the supplied RF energy from the second predetermined voltage level to a third predetermined voltage level with a following voltage ramp up to a fourth predetermined voltage level, wherein the third predetermined voltage level is less than the second predetermined voltage level,
terminate the following ramp up and hold the voltage of the supplied RF energy at a post-ramp voltage level when the output current drops below a pre-determined current threshold, and
end the supply of the RF energy to the electrosurgical instrument after holding the voltage of the supplied RF energy at the post-ramp voltage level for a pre-determined period of time.

12. The electrosurgical generator of claim 11, wherein the controller further signals the RF amplifier to modify the supplied RF energy based on information stored in the electrosurgical instrument, the information including pre-defined output thresholds or shutoff error criteria for the supplied RF energy.

13. The electrosurgical generator of claim 11, wherein the generated information of RF sense circuitry further comprises a root means square (RMS) of the output voltage and the output current, a power of the supplied RF energy, and a phase angle between the output voltage and the output current, and wherein the controller is configured to use one or more of the RMS, power, or phase angle from the RF sense circuitry to signal the RF amplifier to modify the supplied RF energy accordingly.

14. The electrosurgical generator of claim 13, wherein the controller is configured to signal the RF amplifier to terminate the supplied RF energy based on the generated information from the RF sense circuitry that one or more of the phase angle or the output current are above a predetermined error threshold of the one or more pre-determined thresholds.

15. The electrosurgical generator of claim 13, wherein the controller is further configured to terminate the supplied RF energy based on the generated information from the RF sense circuitry being outside an allowable window defining a maximum and minimum value for the generated information.

16. The electrosurgical generator of claim 15, wherein the allowable window is shiftable based on the supplied RF energy.

17. The electrosurgical generator of claim 11, wherein the controller further signals the RF amplifier to modify the supplied RF energy after a pre-determined period of time has elapsed.

18. The electrosurgical generator of claim 13, wherein the controller is configured to signal the RF amplifier to terminate the supplied RF energy based on determination that the generated information from the RF sense circuitry of the power is below a pre-determined termination threshold of the one or more pre-determined thresholds.

* * * * *